United States Patent [19]

Miranda et al.

[11] Patent Number: 5,586,051
[45] Date of Patent: Dec. 17, 1996

[54] CHEMICAL REACTOR FEED CONTROL

[75] Inventors: Ronald E. Miranda; Robert O. Dunn; Martin K. Lyons; Steven D. Bridges; Francis M. Brinkmeyer, all of Bartlesville, Okla.; Michael L. Facker, Sugar Land, Tex.

[73] Assignee: Phillips Petroleum Company, Bartlesville, Okla.

[21] Appl. No.: 393,769

[22] Filed: Feb. 24, 1995

[51] Int. Cl.$^6$ ........................................ G01F 1/00
[52] U.S. Cl. .................. 364/510; 364/500; 364/502; 44/449; 23/306
[58] Field of Search .................. 364/510, 500, 364/501, 502, 550; 44/449; 568/697; 585/401, 415, 501, 639, 701; 23/306

[56] References Cited

U.S. PATENT DOCUMENTS

| | | | |
|---|---|---|---|
| 3,135,807 | 6/1964 | Grasselli et al. | 260/614 |
| 4,290,110 | 9/1981 | Makovec | 364/500 |
| 4,332,590 | 6/1982 | Smith | 23/230 A |
| 4,981,491 | 1/1991 | Harandi et al. | 44/449 X |
| 5,108,719 | 4/1992 | Harandi et al. | 422/187 |
| 5,118,871 | 6/1992 | Cikat et al. | 568/697 |

*Primary Examiner*—Emanuel T. Voeltz
*Assistant Examiner*—Edward Pipala
*Attorney, Agent, or Firm*—George E. Bogatie

[57] ABSTRACT

In a process for manufacture of a chemical product, a reactive hydrocarbon feedstream, which varies in composition of the reactive component, is combined with a compatible but unreactive hydrocarbon feedstream to form a blended hydrocarbon stream which is then combined with a reactive alcohol stream of stable concentration of its reactive component, to form a complete feedstream to the reactor. A desired ratio of relative reactant concentrations in the complete feedstream to the reactor is maintained by a control system which maintains a stable concentration in the blended hydrocarbon stream by manipulating flow rate of the unreactive hydrocarbon feedstream responsive to a concentration measurement in the blended hydrocarbon stream. Flow ratio control is then applied to maintain a desired ratio of reactants in the complete feedstream for the reactor by calculating a flow ratio of the blended hydrocarbon stream to the reactive alcohol feedstream. The calculated flow ratio is the process variable input to a manually set ratio controller which manipulates the flow rate of the reactive alcohol feedstream responsive to the flow ratio.

8 Claims, 2 Drawing Sheets

5,586,051

CHEMICAL REACTOR FEED CONTROL

This invention relates to process control and more particularly to controlling a ratio of at least two reactants flowing to a chemical reactor. In another aspect this invention relates to method and apparatus for feed control to a chemical reactor used in the production of ether.

BACKGROUND OF THE INVENTION

In many chemical processes close control of the ratio of reactants is necessary to ensure that the reaction favors formation of the desired product. For example, it is known that a tert-alkyl ether can be prepared by reacting a primary alcohol with an olefin having a double bond on a tertiary carbon atom, as methanol reacts with isobutylene or isoamylene to form respectively methyl tert-butyl ether (MTBE) or tertamyl methyl ether (TAME). The use of excess of methanol, however, renders the purification of ethers very expensive because of the formation of azeotropes, with the resulting difficulties in distillation of reaction effluent. Many etherification processes utilize feedstreams which are produced by some previous process and are often delivered directly to the ether reactor from a process such as a cracker unit or a dehydrogenation unit in the same or a nearby plant. Under such conditions reactive olefin constituents in the olefin feedstream may be present in variable concentrations due to process variations associated with its production in the previous process. Regardless of such variations it is desired to maintain a close ratio of olefin and alcohol reactants flowing to the ether reactor. Control in such a manner is both more in need and more difficult where the reactant component is present in a feedstream in a relatively low concentration and/or subject to wide variations in concentration.

In an etherification process individual feedstreams of reactive olefin and alcohol are provided to a mixer with the mixed stream fed to the reactor. As used herein an individual reactant stream is a stream containing at least one reactant but not all of the reactants required for a desired reaction. Feedstreams containing unreactive hydrocarbons such as isobutane, herein called lean feedstreams, may also be advantageously employed in the etherification process. For example, a lean feed supplied to the reactor along with the individual reactant streams can aid in the separation steps following the reaction. In the past typical control approaches for maintaining a constant concentration ratio of olefin to alcohol in the reactor feedstream relied on independently controlling the flow rate of the olefin containing feedstream to a flow set point. Changes in concentration of reactive olefin in the olefin containing stream, which would cause a variation in the olefin to alcohol concentration ratio in the reactor feed, are detected by analyzing the mixed feedstream to determine the actual ratio of olefin/alcohol, and then manipulating the individual alcohol stream to avoid a change in the ratio. While the above described control method which manipulates the flow of one or more individual feedstreams in response to measured analysis from a mixed feedstream has proven effective for controlling the olefin to alcohol concentration ratio, it is subject to certain limitations. For example, the analysis of a mixture containing alcohol and olefin components is complex and the analyzer is difficult to calibrate. Further the analysis equipment is difficult to maintain because of the alcohol present in the sample.

It is thus an object of this invention to reduce the cost for recovery of unreacted constituents in a reactor effluent stream.

Another object is to continuously control the flow of each reactive component in a mixed feedstream, with fixed ratios between reactive components, without measuring concentration of each reactive component in the mixed stream.

It is a more specific object of this invention to maintain a desired isoolefin to alcohol ratio in a feedstream to an ether reactor.

It is still another object is to improve efficiency in a process for producing a high purity ether product.

SUMMARY OF THE INVENTION

According to the present invention the foregoing and other objects are obtained by a method and apparatus for controlling reactor feed. The reactor feed is made up by first combining a reactive olefin stream, which is subject to variation in concentration of the reactive olefin, and a lean hydrocarbon feedstream in a first mixer to form a mixed hydrocarbon feedstream. The mixed hydrocarbon feedstream is then combined with a reactive alcohol feedstream, which has a known and stable reactant concentration, in a second mixer to form the complete feedstream for the reactor. The desired ratio of reactive components in the complete feedstream to the reactor is achieved by measuring the concentration of reactive olefin in the mixed hydrocarbon stream upstream of the mixing junction for the alcohol feedstream, and then manipulating the flow rate of the lean hydrocarbon stream to maintain a desired concentration of reactive olefin in the mixed hydrocarbon stream. Flow ratio control is then applied to maintain a desired ratio of reactive olefin to alcohol in the complete reactor feedstream by calculating a flow ratio of the mixed hydrocarbon stream, of controlled concentration, to the individual alcohol stream which has a stable concentration of its reactive component. The calculated flow ratio is the process variable input to a manually set ratio controller which manipulates the flow rate of the reactive alcohol feedstream.

Other objects and advantages of the invention will be apparent from the foregoing brief description of the invention and the claims as well as the detailed description of the drawings in which:

DESCRIPTION OF THE PREFERRED EMBODIMENT

Figure 1:
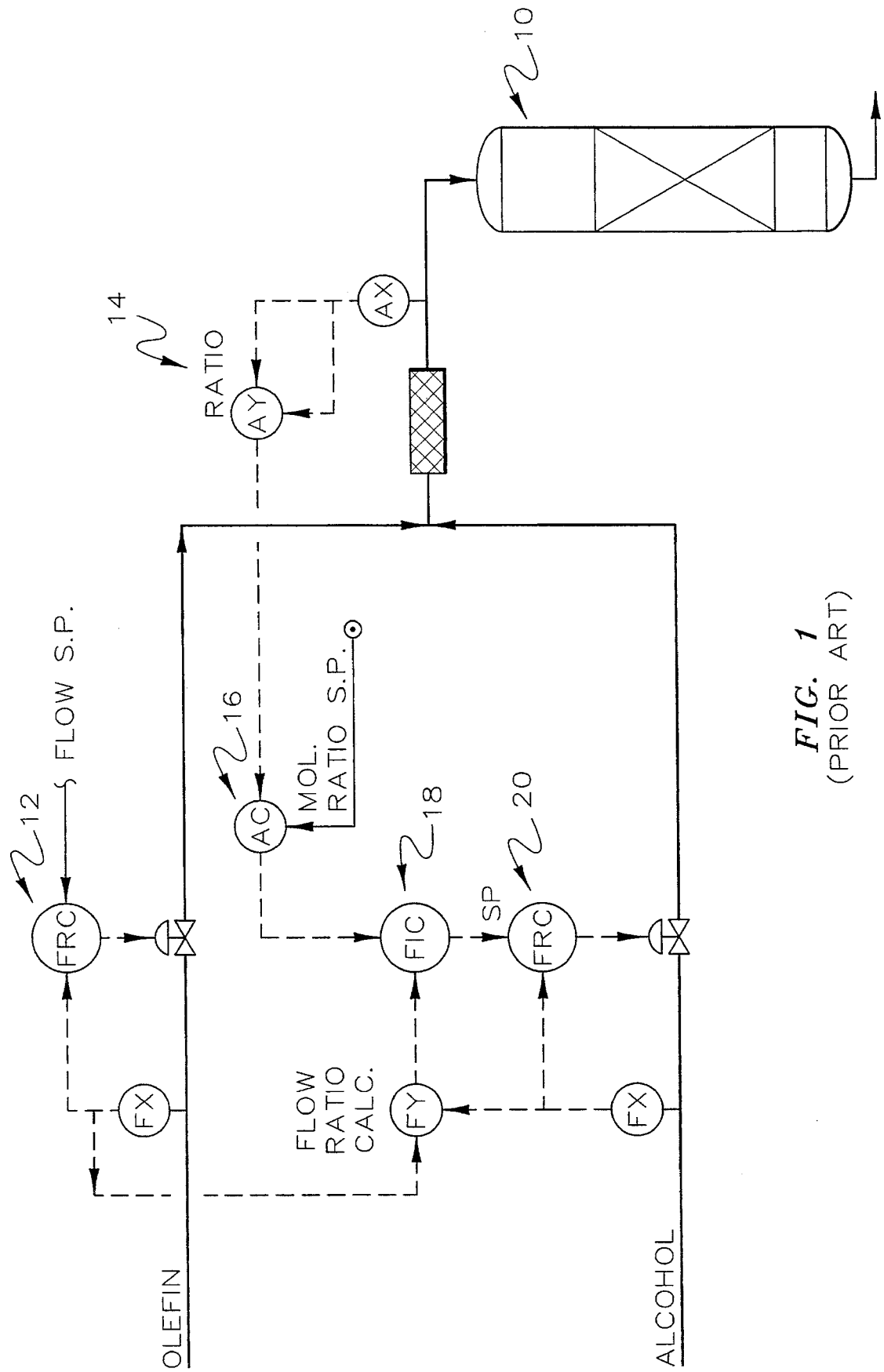
FIG. 1 is a prior art schematic illustrating blending control of two chemical components.

The invention is illustrated and described in terms of a process for the manufacture of methyl tert-butyl ether. The invention, however, is applicable to other manufacturing processes where it is desirable to control the ratio of reactants flowing to the reactor.

Essentially only two reactants, methanol and isobutylene are required to produced methyl tert-butyl ether. However, the blending control of this invention is applicable to the blending of more than two reactant streams.

Although the invention is illustrated and described in terms of a specific control system for feed control for the reactor, the invention is also applicable to different types and configurations of reactors which require blended feedstreams.

Dash lines, which designate signal lines in the drawings, are electrical or pneumatic in this preferred embodiment. However, the invention is also applicable to mechanical, hydraulic, or other signal means for transmitting information. In almost all control systems some combination of these types of signals will be used. However, the use of any other type of signal transmission, compatible with the process and equipment in use is within the scope of the invention.

The controller shown may use various modes of control such as proportional, proportional-integral, proportional-derivative, or proportional-integral-derivative. In this preferred embodiment, proportional-integral controllers are preferred but any controller capable of accepting two input signals and producing a scaled output signal, representative of the comparison of the two input signals, is within the scope of this invention. The operation of proportional-integral controllers is well known in the art. The output control signal of a proportional-integral controller may be represented as $$S = K_1 e + K_2 \int e \, dt$$

where:
  S=output control signal
  e=error between two input signals
  $K_1$ and $K_2$=constants The scaling of an output signal by a controller is well known in control systems art. Essentially the output of a controller may be scaled to represent any desired factor or variable. An example of this is where a desired pressure and an actual pressure are compared in a controller. The output of the controller could be a signal representative of a desired change in the flow rate of some gas to make the desired and actual pressures equal. On the other hand, the same output signal could be scaled to represent a percentage or could be scaled to represent a temperature change required to make the desired and actual pressures equal. If the controller has an output that can range from 0–10 volts, which is typical, then the output signal could be scaled so that an output signal of 5 volts corresponds to 50 percent of some specified flow rate or some specified temperature.

The various transducing means used to measure parameters which characterize the process and the various signals generated thereby may take a variety of forms or formats. For example, the control elements of this system can be implemented using electrical analog, digital electronic, pneumatic, hydraulic, mechanical, or other similar types of equipment or combinations of one or more such equipment types.

The presently preferred embodiment of the invention utilizes distributed control in which the blending of feed components is managed by its own digital computer/controller, with the whole plant interconnected to form a single entity by a communication systems commonly known as data highways.

The distributed control system is used in the preferred embodiment of this invention to calculate the required control signals based on measured process variables and parameters as well as set points supplied to the control system. However, any computer control system having software that allows operation in a real time environment for reading values of external variables and transmitting signals is suitable for use in this invention.

Signal lines are also utilized to represent the results of calculations carried out in a digital computer and the term "signal" is utilized to refer to such results. Thus the term signal is used not only to refer to electrical currents or pneumatic pressures but it is also used to refer to binary representations of a calculated or measured value. The apparatus and method of the invention can accordingly be implemented using a wide variety of specific equipment available to and understood by those skilled in the process control art.

Referring now to FIG. 1 there is shown a conventional blending feed control for an ether reactor generally indicated at 10. Details of the process flow of material to the reactor will be more fully described in reference to FIG. 2 hereinafter. In this conventional control system of FIG. 1 an analyzer system generally indicated at 14, measures concentration of two reactants in the mixed feedstream and calculates a concentration ratio. The measured concentration ratio is compared to a ratio set point in the analyzer controller generally shown at 16, with the outputted analyzer control signal resetting a flow ratio controller which is generally shown at 18. The output of the flow ratio controller is used to reset a flow controller for the reactant stream having the most stable concentration to thereby maintain the desired analysis ratio shown at 16.

Figure 2:
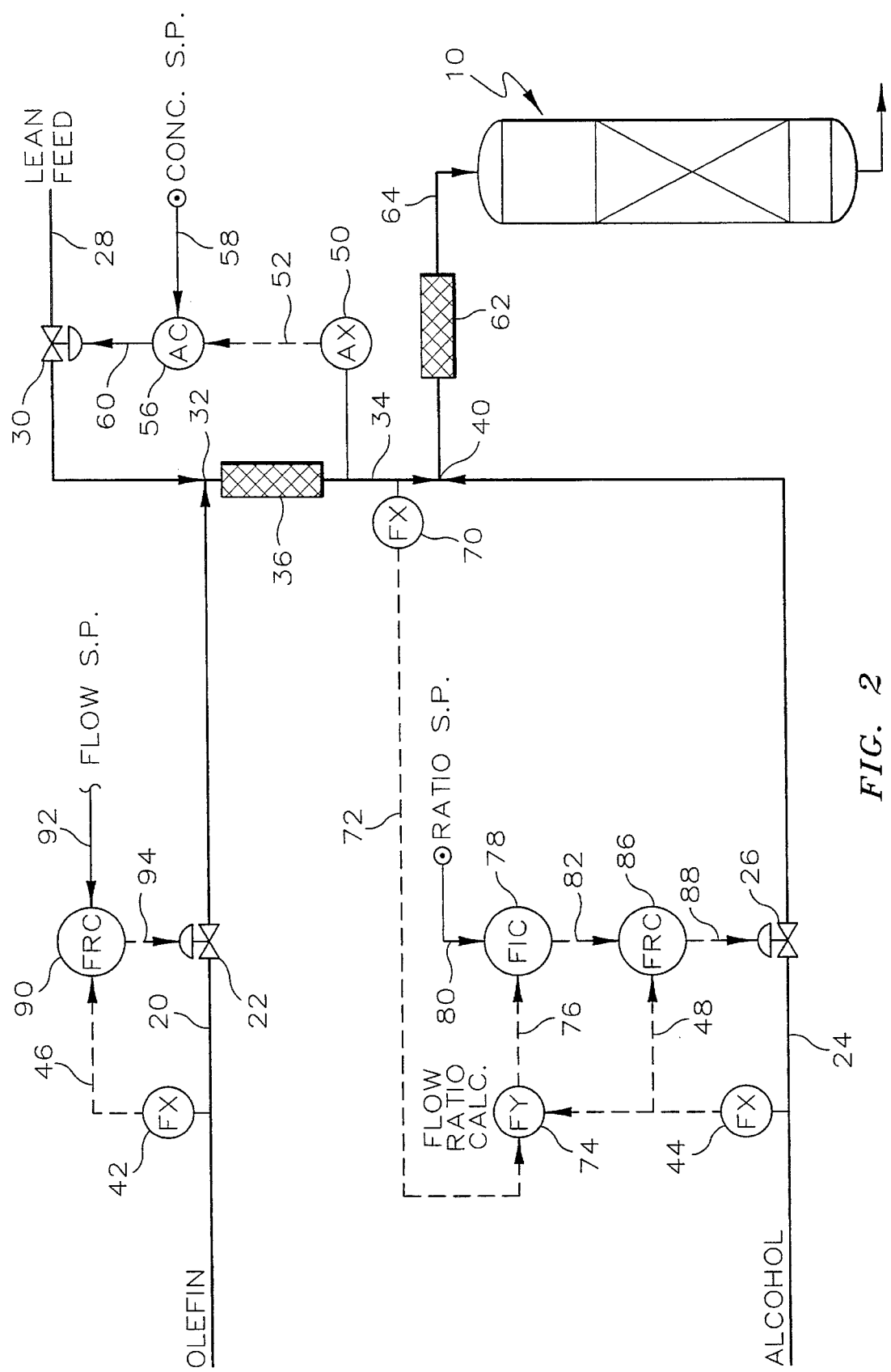
FIG. 2 is a schematic illustrating blending control of two reactive chemical components according to the invention.

Referring now to FIG. 2, there is illustrated process feed flow which includes two individual reactant stream plus a lean feed stream, and which is controlled according to this invention. A first conduit 20 having a flow control valve 22 associated therewith, a second feed conduit 24 having a flow control valve 26 associated therewith and a third conduit 28 having a flow control valve 30 associated therewith are shown. The conduits 20 and 28 are adapted to provide flow of hydrocarbon feedstock material through the associated valves 22 and 30 to a junction point 32 where they are combined to form a combined hydrocarbon feedstream flowing in conduit 34. A suitable means for mixing, such as a static mixer shown at 36, is provided to insure that the material flowing through conduit 34 is substantially homogenous. The conduit 24 provides flow of individual feedstock material through associated valve 26 to a mixing junction 40.

In the preferred embodiment illustrated, the material carried in conduit 20 is a stream containing isobutylene such as e.g., a butane-butylene stream from a cracking unit which contains from about ten to about twenty-five percent of the reactive isobutylene component. In such a stream, the isobutylene content is often relatively low and generally varies even from hour to hour. Alternately, the material carried in conduit 20 is a stream containing isobutylene from a dehydrogenation unit which contains up to about forty percent of the reactive isobutylene, but which isobutylene concentration may also vary. The feed material carried in conduit 24 is methanol, which is delivered from bulk storage and is therefore not subject to uncontrollable variations in overall composition or in methane content. The feed material carried in conduit 34 contains the reactive hydrocarbon such as isobutylene, and this stream is combined with reactive alcohol feed at junction 40. A suitable mixing device such as a static mixer shown at 62 is provided to insure that the material flowing in conduit 64 is substantially homogeneous before entering the reactor 10.

Operably associated with each of conduits 20 and 24 is a respective flow transducer 42 and 44, each of which produces a respective flow signal 46 and 48 which is representative of the volume flow rate of feed material carried through the conduits with which it is associated.

Analysis transducer 50 is adapted to take a sample of fresh process feed material from the conduit 34 and to deliver, in response to the analysis of the reactant containing stream, an isobutylene concentration signal 52 which is representative of the volume fraction of isobutylene in the fresh feed flowing through conduit 34.

Signal 52 is provided as a process variable input to analyzer controller 56. Analyzer controller 56 is also provided with a set point signal 58 which is representative of the desired isobutylene concentration of the mixed hydrocarbon stream flowing in conduit 34. This desired concentration is one which is generally less than the minimum anticipated concentration of the reactive component of the material flowing in conduit 20.

In response to signals 52 and 58 analyzer controller 56 provides a output signal 60 which is responsive to the difference between signals 52 and 58. Signal 60 is scaled so as to be representative of the position of control valve 30 which is operably located in conduit 28, required to maintain the actual isobutylene concentration of the feed material flowing in conduit 34 substantially equal to the desired concentration represented by signal 58. Signal 60 is provided from the analyzer controller 56 as a control signal for the control valve 30, and the control valve 30 is manipulated in response thereto.

Flow transducer 70 which is operably located in conduit 34 provides an output signal 72 which is representative of the flow rate of the material in conduit 34, which is the mixed hydrocarbon feedstream. Signal 72 is provided as an input to the flow ratio calculation or arithmetic block 74 which is associated with the distributed digital control system. Also provided as an input to calculation block 74 is signal 48 which, as previously noted, is representative of the flow rate of material in conduit 24, which is the individual alcohol reactant. In response to signals 72 and 48 calculation block 74 provides an output signal 76 which is representative of the flow ratio of reactive isobutylene flowing in conduit 34 and of reactive alcohol flowing in conduit 24. Signal 76 is provided as a process variable input to flow ratio controller 78.

Also provided to flow ratio controller 78 is a manual set point signal 80 which is representative of the desired flow ratio. This desired flow ratio is a flow ratio that will realize about a 1:1 mol ratio of reactive components flowing to reactor 10 through the mixer 62 and conduit 64.

In response to signals 76 and 80 ratio controller 78 provides an output signal 82 which is responsive to the difference between signals 76 and 80. Signal 82 is scaled to be representative of the flow rate of reactive alcohol required to maintain the ratio represented by signal 76 substantially equal to the desired ratio represented by signal 80. Signal 82 is provided from flow ratio controller 78 as a set point input to flow controller 86. In response to signals 48 and 82 flow controller 86 provides an output signal 88 which is responsive to the difference between signals 48 and 82. Signal 86 is scaled to be representative of the position of control valve 26 required to maintain the actual flow in conduit 24 substantially equal to the desired flow represented by signal 82. Signal 88 is provided to control valve 26 and control valve 26 is manipulated in response thereto.

The present invention encompasses a feed forward control scheme in which changes in reactant composition, which would change the isobutylene to methanol ratio of the complete feedstream to the reactor, are detected by measurements ahead of the mixing junction 40, and accordingly are made without waiting for a change to occur in the complete feedstream to the reactor. Corrections are made by manipulating the flow rate of the lean feed carried in conduit 28, and the alcohol reactant feedstream flowing in conduit 24.

The control scheme is completed with the addition of flow controller 90 which receives a variable signal 46 representative of the actual flow rate in the reactive feedstream 20, and a set point signal 92 which is representative of a desired flow rate for feedstream 20. In response to signals 46 and 92 flow controller 90 provides an output signal 94 which is responsive to the difference between signals 46 and 92. Signal 94 is scaled to be representative of the position control valve 22 required to maintain the actual flow rate in feedstream 20 substantially equal to the desired flow rate represented by signal 92 and control valve 22 is manipulated in response to signal 94.

The invention had been described in terms of a presently preferred embodiment as illustrated in FIG. 2. Specific components which can be used in the practice of this invention as illustrated in FIG. 2, such as flow transducers and analyzer transducers, computer process control equipment are each well known, commercially available control components such as are described at length in Perry's Chemical Engineering Handbook, Sixth Edition, Chapter 22.

While the invention had been described in terms of the presently preferred embodiment, reasonable variations and modifications are possible by those skilled in the art within the scope of the described invention and the appended claims thereto.

That which is claimed:

1. Apparatus comprising:

a reactor;

a first mixer for combining two fluid streams;

means for supplying a first feedstream containing a first hydrocarbon reactant to an inlet of said first mixer, wherein said first reactant is subject to variations in concentration in said first feedstream;

means for maintaining a desired flow rate for said first feedstream;

means for supplying a second feedstream containing unreactive hydrocarbon material to said inlet of said first mixer;

means for providing a mixed hydrocarbon feedstream from the outlet of said first mixer;

a second mixer for combining two fluid streams;

means for supplying a third feedstream containing a second reactant to an inlet of said second mixer, wherein said second reactant is essentially stable in concentration in said third feedstream;

means for providing said mixed hydrocarbon feedstream to said inlet of said second mixer;

means for providing a complete feedstream for said reactor from the outlet of said second mixer to a feed inlet of said reactor;

a control valve operably located in said second feedstream;

means for establishing a first signal representative of the concentration of said first reactant in said mixed hydrocarbon feedstream;

means for establishing a second signal representative of the desired concentration of said first reactant in said mixed hydrocarbon feedstream;

means for establishing a third signal responsive to the difference between said first signal and said second signal, wherein said third signal is scaled to be representative of the position of said control valve required to maintain the concentration of said first reactant in said mixed hydrocarbon feedstream represented by said first signal substantially equal to the desired concentration represented by said second signal;

means for manipulating the flow rate of said second feedstream responsive to said third signal; and means for maintaining the flow rate of said third feedstream at a desired ratio to said mixed hydrocarbon feedstream.

2. Apparatus in accordance with claim 1, wherein said means for maintaining the flow rate of said third feedstream at a desired ratio to said mixed hydrocarbon feedstream comprises:

means for establishing a fourth signal representative of the actual flow rate of said mixed hydrocarbon feedstream;

means for establishing a fifth signal representative of the actual flow rate of said third feedstream;

an arithmetic unit adapted to perform a ratio calculation;

means for providing said fourth signal and said fifth signal to said arithmetic unit, and for establishing a sixth signal representative of the actual ratio of said fourth signal and said fifth signal;

means for establishing a seventh signal representative of the desired ratio of said fourth signal and said fifth signal;

means for comparing said sixth signal and said seventh signal and for establishing an eighth signal responsive to the difference between said sixth signal and said seventh signal, wherein said eighth signal is scaled to be representative of the flow rate of said third feedstream required to maintain the actual ratio represented by said sixth signal substantially equal to the desired ratio represented by said seventh signal; and means for manipulating the flow rate of said third feedstream responsive to said eighth signal.

3. Apparatus in accordance with claim 1, wherein said reactor comprises an ether reactor.

4. Apparatus in accordance with claim 1, wherein said first reactant is a hydrocarbon selected from the group consisting of isobutylene and isoamylene, and said second reactant is an alcohol selected from the group consisting of methanol and ethanol.

5. A method for controlling the concentration ratio of reactants in a feedstream to a reactor, wherein a plurality of reactant containing feedstreams, and a feedstream containing an unreactive hydrocarbon material are combined to form a complete feedstream to said reactor, and wherein a first feedstream containing a first reactant, which comprises a reactive hydrocarbon, is subject to variations in its reactant concentration, and a second feedstream containing a second reactant, which is a reactive alcohol, is essentially stable in its concentration in said second feedstream, said method comprising the steps of:

combining said first feedstream and a third feedstream containing unreactive hydrocarbons to form a mixed hydrocarbon feedstream;

combining said second feedstream and said mixed hydrocarbon feedstream to provide a complete feedstream for said reactor;

establishing a first signal representative of the concentration of said first reactant in said mixed hydrocarbon feedstream;

establishing a second signal representative of the desired concentration of said first reactant in said mixed hydrocarbon feedstream;

establishing a third signal responsive to the difference between said first signal and said second signal, wherein said third signal is scaled to be representative of the position of a control valve in said third feedstream required to maintain the concentration of said first reactant in said mixed hydrocarbon feedstream represented by said first signal substantially equal to the desired concentration represented by said second signal;

manipulating the flow rate of said third feedstream responsive to said third signal; and maintaining the flow rate of said second feedstream at a desired ratio to said mixed hydrocarbon feedstream.

6. A method in accordance with claim 5 wherein said step for maintaining the flow rate of said second feedstream at a desired ratio to said mixed hydrocarbon feedstream comprises:

establishing a fourth signal representative of the actual flow rate of said mixed hydrocarbon feedstream;

establishing a fifth signal representative of the actual flow rate of said second feedstream;

establishing a sixth signal representative of a ratio of said fourth signal and said fifth signal;

establishing a seventh signal representative of the desired ratio of said fourth signal and said fifth signal;

comparing said sixth signal and said seventh signal and establishing an eighth signal which is responsive to the difference between said sixth signal and said seventh signal, wherein said eighth signal is scaled to be representative of the flow rate of said second feedstream required to maintain the actual ratio represented by said sixth signal substantially equal to the desired ratio represented by said seventh signal; and manipulating the flow rate of said second feedstream responsive to said eighth signal.

7. A method in accordance with claim 5, wherein said reactor comprises an ether reactor.

8. A method in accordance with claim 5, wherein said first reactant is a hydrocarbon selected from the group of hydrocarbons consisting of isobutylene and isoamylene, and said second reactant is an alcohol selected from the group of alcohols consisting of methanol and ethanol.

* * * * *